United States Patent [19]

Waketa et al.

[11] Patent Number: 5,069,971

[45] Date of Patent: Dec. 3, 1991

[54] SILANE COUPLING AGENT AND GLASS FIBER PRODUCT FOR LAMINATES

[75] Inventors: Hideharu Waketa; Yoshiharu Suzuki; Motoharu Murakoshi, all of Fukushima; Hideaki Kakiuchi, Saitama; Masuhito Ohgushi, Kumamoto; Kenichi Watanabe; Toshiya Sawai, both of Kanagawa, Japan

[73] Assignees: Nitto Boseki Co., Ltd.; Chisso Corporation, both of Japan

[21] Appl. No.: 432,856

[22] Filed: Nov. 7, 1989

[30] Foreign Application Priority Data

Nov. 8, 1988 [JP] Japan .................................. 63-280417
Aug. 24, 1989 [JP] Japan .................................. 1-216025

[51] Int. Cl.$^5$ ............................................. B32B 17/04
[52] U.S. Cl. .................................... 428/391; 428/392; 428/428; 428/447; 524/588
[58] Field of Search .............. 428/447, 391, 375, 392, 428/428; 524/588; 106/287.23

[56] References Cited

U.S. PATENT DOCUMENTS 4,448,694  5/1984  Plueddemaann ...................... 210/682
4,943,452  7/1990  Itagaki et al. ........................ 428/428

FOREIGN PATENT DOCUMENTS 0136680  4/1985  European Pat. Off. .
0146142  6/1985  European Pat. Off. .

OTHER PUBLICATIONS

Inokuchi et al, "Aminosilane Coupling Agents", Chemical Abstracts, 106, 18807k, 1987.
Pleuddemann, "Cationic Silane Coupling Agents for Thermoplastics", Chemical Abstracts, 77, 6189g, 1972.

Primary Examiner—Merrell C. Cashion, Jr.
Assistant Examiner—D. S. Nakarani
Attorney, Agent, or Firm—Leydig, Voit & Mayer

[57] ABSTRACT

A glass fiber product for laminates is provided having excellent epoxy resin impregnation properties and solvent resistance, high soldering heat resistance, good heat shock resistance and low water adsorption properties, and to a silane coupling agent for providing such a glass fiber product.

The silane coupling agent is prepared by reacting 2.3 to 4.0 mols of a haloalkylalkoxysilane with 1 mol of a diamine having N atoms to which 4 active hydrogen atoms are bound, a silane coupling agent prepared by reacting 1.3 to 3.0 mols of a haloalkylalkoxysilane with 1 mol of a diamine having N atoms to which 3 active hydrogen atoms are bound and to which one alkylsilyl group is bound, or a silane coupling agent prepared by reacting 0.3 to 2.0 mols of a haloalkylalkoxysilane with 1 mol of a diamine having N atoms to which 2 active hydrogen atoms are bound and to which 2 alkylsilyl groups are bound. A silane coupling agent prepared by reacting the diamine with a haloalkylalkoxysilane and a halomethylstyrene is also provided as is a glass fiber product for laminates treated with the above-mentioned silane coupling agent.

17 Claims, No Drawings

SILANE COUPLING AGENT AND GLASS FIBER PRODUCT FOR LAMINATES

BACKGROUND OF THE INVENTION (1) Field of the Invention

The present invention relates to a novel silane coupling agent and a glass fiber product for laminates treated with the silane coupling agent.

(2) Description of the Prior Art

In general, a silane coupling agent has the structure in which a silicon atom simultaneously has an alkoxy group capable of reacting with the surface of an inorganic material and an organic functional group which is reactive or compatible with an organic material, and therefore the silane coupling agent is used as an adhesion improver between the organic and inorganic materials.

For example, the silane coupling agents are widely utilized with the intention of improving mechanical strength, electrical characteristics, water resistance, heat resistance, adhesive properties and the like in the fields of the surface treatment of glass fibers and various inorganic fillers as well as the modification of reinforced plastics, sealants, adhesives and coating materials by adding the silane coupling agent itself to their matrix resins.

Above all, the application of the silane coupling agent to the surface treatment of glass fibers for glass epoxy laminates and the like is one of the applications in which some effects of the silane coupling agent can be most effective.

Examples of conventional surface treating agents suitable for glass fibers, particularly glass fibers for glass epoxy laminates include silane compounds such as 3-aminopropyltriethoxysilane, 3-glycidoxypropyltrimethoxysilane and 3-(N-styrylmethyl-2-aminoethylamino)propyltrimethoxysilane hydrochloride.

In recent years, technical innovation made rapid progress in the field of glass fibers, particularly glass epoxy laminates, and needless to say, these laminates are required to be excellent in epoxy resin impregnation, properties and solvent resistance. Particularly, with the advance of soldering techniques in printed-circuit board-manufacturing processes and manufacturing techniques in multi-layer printed-circuit board-manufacturing processes when glass epoxy laminates are used as printed circuit boards, it is demanded that they have higher heat resistance and lower water absorption properties.

In these days, however, the conventional silane coupling agents scarcely satisfy these requirements, and another silane coupling agent having more excellent functions is desired.

On the other hand, most of the silane coupling agents presently used are high-boiling single compounds manufactured by isolation and purification.

SUMMARY OF THE INVENTION

An object of the present invention is to provide a glass fiber product for laminates having excellent epoxy resin impregnation properties and solvent resistance, high soldering heat resistance, good heat shock resistance and low water absorption properties.

Another object of the present case is to provide a silane coupling agent used to manufacture such a glass fiber product.

Inventors of the present application have intensively conducted research to solve the above-mentioned problems, and as a result, they have found that an aminosilane compound formed by subjecting a diamine compound and a haloalkylalkoxysilane, which are raw materials, to a condensation reaction in a limited ratio or another aminosilane compound formed by the addition reaction of halomethylstyrene to the condensation reaction product can be directly used in the form of various mixtures without undergoing any particular operations of isolation and purification, and that the employment of the above-mentioned aminosilane compound can solve these problems. The present invention has been achieved on the basis of this knowledge.

That is, the present invention is directed to (1) a silane coupling agent prepared by reacting 2.3 to 4.0 mols of a haloalkylalkoxysilane with 1 mol of a diamine having N atoms to which 4 active hydrogen atoms are bound (hereinafter referred to as "diamine A"), (2) a silane coupling agent prepared by reacting 1.3 to 3.0 mols of a haloalkylalkoxysilane with 1 mol of a diamine having N atoms to one of which one alkylsilyl group is bound and to the residual bonds of which 3 active hydrogen atoms are bound (hereinafter referred to as "diamine B").

(3) a silane coupling agent prepared by reacting 0.3 to 2.0 mols of a haloalkylalkoxysilane with 1 mol of a diamine having N atoms to each or either of which 2 alkylsilyl group are bound and to each or either of which 2 active hydrogen atoms are bound (hereinafter referred to as "diamine C"), (4) a silane coupling agent prepared by reacting a halomethylstyrene with a reaction product obtained by reacting 1 mol of the above mentioned diamine A with 2.3 to 3.5 mols of a haloalkylalkoxysilane, a reaction product obtained by reacting 1 mol of the above mentioned diamine B with 1.3 to 2.5 mols of a haloalkylalkoxysilane, or a reaction product obtained by reacting 1 mol of the above mentioned diamine C with 0.3 to 1.5 mols of a haloalkylalkoxysilane, the amount of the aforesaid halomethylstyrene being not more than 80 mol% of mol amounts obtained by subtracting the mols of the used haloalkylalkoxysilane from the mols of the active hydrogen of the used diamine, (5) a process for preparing a silane coupling agent described in any one of the previous paragraphs (1) to (4) which comprises the step of reacting a haloalkylalkoxysilane with a diamine having at least an N atom to which an active hydrogen atom is bound or active hydrogen atoms are bound, while a secondarily produced hydrogen halide is removed by the use of a basic substance which is inert to the raw materials and the reaction product.

(6) a glass fiber product for laminates treated with the silane coupling agent described in any one of the previous paragraphs (1) to (4).

DETAILED DESCRIPTION OF THE INVENTION

A haloalkylalkoxysilane which can be used in the practice of the present invention is preferably a compound represented by the formula

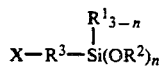

wherein each of $R^1$ and $R^2$ is independently a substituted or unsubstituted alkyl group, an aryl group or an alkenyl group, each of said groups having 1 to 6 carbon atoms, $R^3$ is a straight-chain or branched alkylene group having 1 to 6 carbon atoms, n is 1, 2 or 3, and X is a halogen atom.

Examples of such a haloalkylalkoxysilane compound include 3-chloropropyltrimethoxysilane, 3-chloropropyltriethoxysilane, 3-bromopropyltrimethoxysilane, 3-bromopropyltriethoxysilane, 4-chlorobutyltrimethoxysilane, 4-chlorobutyltriethoxysilane, 3-chloropropylmethyldimethoxysilane, 3-chloropropylmethyldiethoxysilane, 3-bromopropylmethyldimethoxysilane, 3-bromopropylmethyldiethoxysilane, 3-chloropropyldimethylmethoxysilane, 3-chloropropyldimethylethoxysilane, 3-bromopropyldimethylmethoxysilane and 3-bromopropyldimethylethoxysilane.

Examples of the diamine A used in the present invention include primary or secondary ethylenediamine, diaminopropane, diaminobutane, hexamethylenediamine, phenylenediamine, xylylenediamine, diaminobiphenyl, diaminodiphenylmethane and naphthylenediamine.

Examples of the diamine B mentioned above include N-2-aminoethylaminopropylmethyldimethoxysilane, N-2-aminoethylaminopropylmethyldiethoxysilane, N-2-aminoethylaminopropyltrimethoxysilane, N-2-aminoethylaminopropyltriethoxysilane, N-2-aminoethylaminopropyldimethylmethoxysilane, N-2-aminoethylaminopropyldimethylethoxysilane, N-trimethoxysilylpropyldiaminopropane, N-trimethoxysilylpropyldiaminohexane, N-trimethoxysilylpropylphenylenediamine, N-trimethoxysilylpropyldiaminobiphenyl, N-trimethoxysilylpropyldiaminodiphenylmethane and (aminoethylaminomethyl)phenethyltrimethoxysilane.

Examples of the diamine C incude N,N'-bis[3-(trimethoxysilyl)propyl]ethylenediamine, N,N-bis[3-(trimethoxysilyl)propyl]ethylenediamine, N,N'-bis[3-(methyldimethoxysilyl)propyl]ethylenediamine N,N-bis[3-(methyldimethoxysilyl)propyl]ethylenediamine, N,N'-bis[3-(dimethylmethoxysilyl)propyl]ethylenediamine, N,N-bis[3-(dimethylmethoxysilyl)propyl]ethylenediamine, N-[3-(methyldimethoxysilyl)propyl]-N'-[3-(trimethoxysilyl)propyl]ethylenediamine, N-[3-(methyldimethoxysilyl)propyl]-N-[3-(trimethoxysilyl)propyl]ethylenediamine, N,N'-bis[3-(trimethoxysilyl)propyl]diaminopropane, N,N'-bis[3-(trimethoxysilyl)propyl]diaminohexane, N,N'-bis[3-(trimethoxysilyl)propyl]phenylenediamine, N,N'-bis[3-(trimethoxysilyl)propyl]diaminobiphenyl and N,N'-bis[3-(trimethoxysilyl)propyl]diaminodiphenylmethane.

Examples of the halomethylstyrene used in the present invention include chloromethylstyrene, bromomethylstyrene and iodomethylstyrene, but practically methylstyrene chloride is convenient.

The reaction is carried out in a dried organic solvent which is inert to the raw materials.

Examples of the solvent include lower alcohols such as methanol and ethanol, ethers such as tetrahydrofuran and dioxane, and aromatic hydrocarbons such as toluene and xylene. These solvents are preferahly used in a dry state. If a large amount of moisture is contained in the solvent, the alkoxy group of the raw materials and product undergoes hydrolysis in order to form a condensate, with the result that the yield of the desired product deteriorates.

The reaction between the haloalkylalkoxysilane and the diamine A, B or C proceeds on the basis of dehydrodiamine halogenation reaction between an N–H group of the amine and a C–X group (X is a halogen atom) of the haloalkylalkoxysilane.

In order to obtain the excellent coupling agent, it is important that the reaction proceed sufficiently so that the conversion of the raw materials may be 100%. However, the diamine, A, B or C, which is the raw material captures the released hydrogen halide, so that the reactivity of the diamine declines, which impedes the smooth progress of the reaction. In addition, an intermediate in the reaction and the reaction product also capture the hydrogen halide of the by-product. In consequence, when this reaction product is further reacted with the halomethylstyrene, the hydrogen halide which reacts with to the reaction product impedes the reaction with the halomethylstyrene.

Thus, it is necessary to remove the hydrogen halide from the diamine, the intermediate and the reaction product with which it reacts, by a basic material inert to the diamine of the raw material, the intermediate and the reaction product.

It is preferred that this basic material is inert to the raw material diamine, intermediate and reaction product and has a higher basicity than the raw material diamine or the like.

Examples of the basic material include metallic alkoxides such as sodium methylate and sodium ethylate, and organic bases such as triethylamine, triethylenediamine, 1,8-diazabicyclo(5,4,0)undecene-7.

In reacting the haloalkylalkoxysilane with the diamine A, the haloalkylalkoxysilane is used in an amount of 2.3 to 4.0 mols, preferably 2.4 to 3.5 mols per mol of the diamine A. If the amount of the haloalkylalkoxysilane is less than 2.3 mols, a large amount of the raw material diamine A remains in an unreacted state, and the amount of component which can function as the coupling agent decreases. In addition, it is also impossible to obtain any silane coupling agent which can provide the glass fiber product for laminates having excellent epoxy resin impregnation properties and solvent resistance, high soldering heat resistance, good heat shock resistance and low water absorption properties.

In reacting the haloalkylalkoxysilane with the diamine B, the haloalkylalkoxysilane is used in an amount of 1.3 to 3.0 mols, preferably 1.4 to 2.5 mols per mol of the diamine B. If the amount of the haloalkylalkoxysilane is less than 1.3 mols, it is impossible to obtain any silane coupling agent which can provide the glass fiber product for laminates having excellent epoxy resin impregnation properties and the above-mentioned various characteristics.

In reacting the haloalkylalkoxysilane with the diamine C, the haloalkylalkoxysilane is used in an amount of 0.3 to 2.0 mols, preferably 0.4 to 1.5 mols per mol of the diamine C. If the amount of the haloalkylalkoxysilane is less than 0.3 mols, it is impossible to obtain any silane coupling agent which can provide the glass fiber product for laminates having excellent epoxy resin impregnation properties and the above-mentioned various characteristics.

When the haloalkylalkoxysilane is used in an amount more than the moles of the active hydrogen of the diamine, the unreacted haloalkylalkoxysilane remains, which is inconveniently uneconomical and which lowers the concentration of the desired effective component. In this case, it can be presumed that the unreacted haloalkylalkoxysilane is removed by distillation, or the like, but this means is also inconvenient, since a distillation step is required.

Consequently, in reacting the haloalkylalkoxysilane with the diamine A, B or C, it is preferred that the haloalkylalkoxysilane is used in an amount of 4.0, 3.0 or 2.0 mols, respectively, with respect to 1 mol of the diamine A, B or C.

The start of the reaction is made by dissolving the haloalkylalkoxysilane and the diamine A, B or C in the above-mentioned solvent, or adding dropwise the haloalkylalkoxysilane to the diamine A, B or C. This reaction proceeds at a temperature of 60° C. or more, but the preferable range of the reaction temperature is from 100° to 180° C.

As the reaction proceeds, the secondarily produced hydrogen halide reacts with the raw materials and product. Therefore, as the reaction proceeds a reaction rate decreases gradually until the reaction attains equilibrium.

At this point the basic material is added to the system in an amount corresponding to that of the secondarily produced hydrogen halide in order to remove the hydrogen halide from the raw materials and product, whereby the reaction rate can be recovered.

In this way, the steps of the reaction and the removal of the hydrogen halide by the basic material are repeatedly carried out until the conversion of the raw materials has reached substantially 100%, and afterward the reaction is brought to an end.

Another novel silane coupling agent comprising a composition of various compounds is a silane coupling agent prepared by reacting a halomethylstyrene with a reaction product obtained by reacting 1 mol of the diamine A with 2.3 to 3.5 mols of a haloalkylalkoxysilane, a reaction product obtained by reacting 1 mol of the diamine B with 1.3 to 2.5 mols of a haloalkylalkoxysilane, or a reaction product obtained by reacting 1 mol of the diamine C with 0.3 to 1.5 mols of a haloalkylalkoxysilane, the amount of the aforesaid halomethylstyrene being not more than 80% of the mol amounts given by subtracting the mols of the haloalkylalkoxysilane used from the mols of the active hydrogen of the diamine used (the reaction product obtained by reacting the diamine A, B or C with the haloalkylalkoxysilane in such a ratio, which is to be reacted with the halomethylstyrene, will be hereinafter referred to as "reaction product F").

In reacting the haloalkylalkoxysilane with the diamine A, the haloalkylalkoxysilane is used as a raw material in an amount of 2.3 to 3.5 mols, preferably 2.4 to 3.5 mols per mol of the diamine A. If the amount of the haloalkylalkoxysilane is less than 2.3 mols, it is also impossible to obtain any silane coupling agent which can provide the glass fiber product for laminates having excellent epoxy resin impregnation properties and solvent resistance, high soldering heat resistance, good heat shock resistance and low water absorption properties. Inversely, if the amount of the haloalkylalkoxysilane is more than 3.5 mols, the addition amount of the halomethylstyrene is deficient at the time of the subsequent reaction with the halomethylstyrene.

In reacting the haloalkylalkoxysilane with the diamine B, the haloalkylalkoxysilane is used in an amount of 1.3 to 2.5 mols, preferably 1.4 to 2.5 mols per mol of the diamine B. If the amount of the haloalkylalkoxysilane is less than 1.3 mols, it is impossible to obtain any silane coupling agent which can provide the glass fiber product for laminates having excellent epoxy resin impregnation properties and the above-mentioned various characteristics. Inversely, if the amount of the haloalkylalkoxysilane is more than 2.5 mols, the addition amount of the halomethylstyrene is deficient at the time of the subsequent reaction with the halomethylstyrene.

In reacting the haloalkylalkoxysilane with the diamine C, the haloalkylalkoxysilane is used in an amount of 0.3 to 1.5 mols, preferably 0.4 to 1.5 mols per mol of the diamine C. If the amount of the haloalkylalkoxysilane is less than 0.3 mols, it is impossible to obtain any silane coupling agent which can provide the glass fiber product for laminates having excellent epoxy resin impregnation properties and the above-mentioned various characteristics. Inversely, if the amount of the haloalkylalkoxysilane is more than 1.5 mols, the addition amount of the halomethylstyrene is deficient at the time of the subsequent reaction with the halomethylstyrene.

The start of the reaction is made by dissolving the haloalkylalkoxysilane and the diamine A, B or C in the above-mentioned solvent, or adding dropwise the haloalkylalkoxysilane to the diamine A, B or C. The reaction proceeds at a temperature of 60° C. or more, but the preferable range of the reaction temperature is from 100° to 180° C.

As the reaction proceeds,, the secondarily produced hydrogen halide reacts with the raw materials and product. Therefore, time of the reaction proceeds, a reaction rate decreases gradually until the reaction attains equilibrium, as described above.

At this point a basic substance is added to the system in an amount corresponding to that of the secondarily produced hydrogen halide in order to remove the hydrogen halide from the raw materials and product, whereby the reaction rate can be recovered.

In this way, the two processes of the reaction and the removal of the hydrogen halide by the basic material are repeatedly carried out until the conversion of the raw materials has reached substantially 100%, and afterward the reaction is brought to an end. In consequence, the desired reaction product F is obtained.

In the reaction between the reaction product F and the halomethylstyrene, the amount of halomethylstyrene is preferably not more than 80 mol% of the mol amounts given by subtracting mols of the haloalkylalkoxysilane used from mols of the active hydrogen of the diamine used. If the amount of the halomethylstyrene is more than 80% the product manufactured therefrom is difficult to dissolve in water when the product is used in the form of an aqueous solution. In addition, the use of too much of the halomethylstyrene is uneconomical.

The reaction is begun by dissolving the reaction product F in the above-mentioned solvent and then adding dropwise the halomethylstyrene to the resulting solution. As the addition proceeds, the temperature of the reaction system rises gradually from exothermic heat produced. The reaction is performed in the temperature range of from room temperature to 100° C., preferably 30° to 80° C. for a period of 1 to 10 hours (the resulting reaction product will be hereinafter referred to as "reaction product G").

In the reaction product obtained by the reaction between the haloalkylalkoxysilane and the diamine A, B or C, and in the reaction products F and G, many kinds of compounds are contained. The reaction product F or the reaction product obtained by the reaction between the haloalkylalkoxysilane and the diamine A, B or C is considered to be a composition of various molecules in which 0 to 4 alkoxysilylalkyl groups are bound to 1 molecule of the diamine A, B or C. Furthermore, the reaction product G is considered to be a composition of various molecules in which 0 to 4 halomethylstyrenes are bound to 1 molecule of diamine contained in the reaction product F.

The constitutional ratio of the various products depends upon a blend ratio of the raw materials and reaction conditions, and therefore it is necessary to optimize the constitutional ratio for each application so as to obtain good performace.

Owing to this optimization, when used as a surface treating agent, the silane coupling agent of the present invention can be adapted to changes in treatment conditions.

The silane coupling agent of the present invention is useful as the surface treating agent for inorganic materials in common with usual silane coupling agents. Examples of the inorganic material to which the silane coupling agent of the present invention can be applied include naturally occurring minerals and artificially synthesized minerals such as glass, silica, alumina, talc, kaolin clay, mica, calcium carbonate, potassium titanate, silas, aluminum hydroxide, zeolite, titanium oxide, asbestos, silicon nitride and iron oxide. In addition, the silane coupling agent of the present invention can also be applied to metals such as stainless steel, aluminum and copper which are oxidized and covered with an oxide layer.

It has been found that a glass fiber product for printed circuit boards having excellent epoxy resin impregnation properties and solvent resistance, high soldering heat resistance, good heat shock resistance and low water absorption properties can be obtained by treating the glass fiber product itself with the silane coupling agent described in any one of the previous paragraph (1) to (4).

The amount of the silane coupling agent used for this treatment depends upon the kind of glass fiber product, but it is from 0.2 to 3.0% (% by weight; the same shall apply hereinafter), preferably 0.5 to 2.0% in terms of the concentration of a treating solution, and in other words, the amount of the silane coupling agent is from 0.06 to 0.50%, preferably 0.10 to 0.35% in terms of its adhered amount on the glass fiber.

In the surface treatment, the silane coupling agent is usually used in the form of an aqueous solution, but it can also be used in the form of a mixed solution of water and an organic solvent such as an alcohol, a ketone or a glycol ether.

In that case, a pH of the solution containing the silane coupling agent is 4 or less, preferably in the range of from 2 to 4. As the organic solvent, methanol is particularly preferable, and the concentration of the silane coupling agent in the solution is preferably from 30 to 40%. The other steps for the surface treatment of the glass fiber can be carried out in a usual manner. That is, an application step is done by an immersion step or the use of a roll coater or by means of spraying or the like at ordinary temperature.

As the glass fiber, E glass (non-alkali fiber glass for electric uses) is particularly preferable, but S glass (high-strength glass), D glass (low-dielectric glass) and quartz glass can be also utilized. Furthermore, examples of the glass fiber product include glass cloth, glass tape, glass yarn, glass roving, glass mat, glass paper and glass powder.

The silane coupling agent of the present invention is excellent in affinity for and compatibility with thermosetting resins and thermoplastic resins. Therefore, when the surface of the glass fiber product is treated with the silane coupling agent, the affinity, i.e. adhesion between the glass fiber product and the above-mentoned matrix resin can be improved.

This reason would be as follows: A general conventional silane coupling agent contains, as the main component, a compound having one silyl group [—Si(OR)$_3$] in its molecule, but the silane coupling agent of the present invention contains, as the fundamental component, the reaction product obtained by reacting each diamine with the haloalkylalkoxysilane in a specific molar ratio. That is, the silane coupling agent of the present invention is basically, for example, a silane coupling agent prepared by reacting 2.3 to 4.0 mols of a haloalkylalkoxysilane with 1 mol of a diamine having N atoms to which 4 active hydrogen atoms are bound, a silane coupling agent prepared by reacting 1.3 to 3.0 mols of a haloalkylalkoxysilane with 1 mol of a diamine having N atoms to one of which one alkylsilyl group is bound and to the residual bonds of which 3 active hydrogen atoms are bound or a silane coupling agent prepared by reacting 0.3 to 2.0 mols of a haloalkylalkoxysilane with 1 mol of a diamine having N atoms to each or either of which 2 alkylsilyl groups are bound and to each or either of which 2 active hydrogen atoms are bound.

Therefore, the silane coupling agent of the present invention contains, as the main components, the reaction product having 2 silyl groups, the reaction product having 3 silyl groups and the reaction product having the 4 silyl groups, and if the silane coupling agent of the present invention is regarded as a mixture of these reaction products, 2.3 or more silyl groups are contained in one molecule of the agent.

With regard to the silane coupling agent of the present invention, when —Si(OR)$_3$ is hydrolyzed to —Si(OH)$_3$, the group which reacts with the silanol group on the surface of the glass fiber is present 2.3 times or more as much as in the conventional silane coupling agent. Additionally, when a siloxane bond is formed, a crosslinking density in the molecular structure of the siloxane is heightened 2.3-fold or more by the reactive group which is present 2.3 times or more than in the conventional one, so that a closer network structure is formed. In consequence, water resistance and adhesive strength increase, and heat resistance also improves.

If the molar ratio between the diamine and the haloalkylalkoxysilane is lower than the above-mentioned range, for example, if the molar ratio of the haloalkylalkoxysilane to the diamine having N atoms to which 4 active hydrogen atoms are bound is less than 2.3, a sufficient effect cannot be obtained. This fact indicates that when the number of the silyl groups present in one molecule of the diamine is 2 on the average, the closer network structure can scarcely be obtained.

Also, when the haloalkylalkoxysilane which reacts with the diamine is a compound having the formula

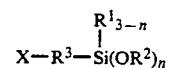

wherein each of $R^1$ and $R^2$ are independently a substituted or unsubstituted alkyl group an aryl group or an alkenyl group each having 1 to 6 carbon atoms, $R^3$ is a straight-chain or branched alkylene group having 1 to 6 carbon atoms, n is 1, 2 or 3, and X is a halogen atom,
a similar effect can be obtained as compared with the case where the silyl group is -Si(OR)3.

The forth silane coupling agent of the present invention to which the halomethylstyrene is added has a styryl group in its molecule, and therefore this type of silane coupling agent has increased affinity for and compatibility with a matrix resin. In consequence, a greater effect can be expected.

The silane coupling agent of the present invention is a mixture of the reaction products in which isomers and homologues are present, and therefore the constitutional ratio of the products can be adjusted by optimizing the blend ratio of the raw materials and reaction conditions so as to adapt changes in preparation conditions of a treating agent, treatment conditions and the like at the time when the product is used as a surface treating agent.

An inorganic material treated by the silane coupling agent of the present invention can be mixed with a thermosetting resin such as epoxy resin or polyimide resin and then thermally cured, thereby obtaining a strong composite material.

In particular, a glass fiber base material treated with the silane coupling agent of the present invention can have excellent affinity for and compatibility with a matrix resin as well as improved adhesion to the matrix resin. Therefore, printed-circuit boards manufactured by using the glass fiber base material of the present invention are excellent in heat resistance such as soldering heat resistance or heat shock resistance, water absorption properties and solvent resistance.

EXAMPLES

Now, the present invention will be described in detail with reference to examples, but the scope of the present case should not be limited to these examples.

In the examples and comparative examples, mols of each component in a mixture are expressed in terms of an average composition.

Example 1

In a 10-liter flask, the inner atmosphere of which was previously replaced with dried nitrogen, were placed 1,606 g (7.23 mols) of N-2-aminoethylaminopropyltrimethoxysilane, 2,440 g (12.3 mols) of 3-chloropropyltrimethoxysilane and xylene, and reaction was then performed with stirring at 130° C. for 5 hours. Next, 1,630 g of a sodium methylate solution (28% methanol solvent; in the following, this solvent was similarly used) was added dropwise thereto over about 4 hours. Afterward, the reaction was further continued for 5 hours, and 740 g of the sodium methylate solution was then added dropwise thereto again over 2 hours to perform the reaction. During this operation vaporized methanol was distilled off in order to maintain the desired reaction temperature.

After completion of the reaction, secondarily produced sodium chloride was removed from the system, whereby a light brown reaction solution was obtained.

This reaction solution was then analyzed by gas chromatography, and it was confirmed that the raw materials were consumed. According to silver nitrate titration, it was found that the amount of chlorine present was 240 ppm, which means that most of the sodium chloride by-product was removed therefrom.

Furthermore, methanol and xylene were removed from this reaction solution in order to obtain a reaction product. The latter was then analyzed by NMR, and it was confirmed that the product had the following structure.

Results of NMR analysis:

|  | (ppm) | Intensity Ratio Found | Calcd. |
|---|---|---|---|
| Si—C$\underline{H}_2$— | 0.6 | 2.0 H | 2.0 H |
| Si—C$\underline{H}_2$—C$\underline{H}_2$— + >N$\underline{H}$ | 1.5 | 2.7 H | 2.5 H |
| SiCH$_2$CH$_2$—C$\underline{H}_2$— + >NC$\underline{H}_2$C$\underline{H}_2$N< | 2.4 | 3.8 H | 3.5 H |
| Si—O—C$\underline{H}_3$ | 3.5 | 8.5 H | 9.0 H |

Structural formula:

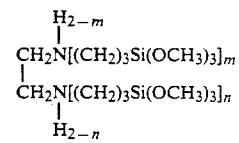

wherein m+n=2.7.

Example 2

In a 10-liter flask, the inner atmosphere of which was previously replaced with dried nitrogen, were placed 1,700 g (8.25 mols) of N-2-aminoethylaminopropylmethyldimethoxysilane, 2,110 g (11.5 mols) of 3-chloropropylmethyldimethoxysilane and xylene, and reaction was then performed with stirring at 130° C. for 5 hours. Next, 1,560 g of a sodium methylate solution was added dropwise thereto over about 4 hours. Afterward, the reaction was further continued for 5 hours, and 667 g of the sodium methylate solution was then added dropwise thereto again over 2 hours to perform the reaction. During this operation, vaporized methanol was distilled off in order to maintain the desired reaction temperature.

After completion of the reaction, secondarily produced sodium chloride was removed from the system, whereby a light brown reaction solution was obtained.

This reaction solution was then analyzed by gas chromatography, and it was confirmed that the raw materials were consumed. According to silver nitrate titration, it was found that the amount of chlorine present was 210 ppm, which means that most of the sodium chloride by-product was removed therefrom.

Furthermore, methanol and xylene were removed from this reaction solution in order to obtain a reaction product. The latter was then analyzed by NMR, and it was confirmed that the product had the following structure.

Results of NMR analysis:

|  | (ppm) | Intensity Ratio Found | Calcd. |
|---|---|---|---|
| Si—C$\underline{H}_3$ | 0.1 | 2.9 H | 3.0 H |
| Si—C$\underline{H}_2$— | 0.6 | 2.0 H | 2.0 H |
| Si—C$\underline{H}_2$—C$\underline{H}_2$— + >N$\underline{H}$ | 1.5 | 2.8 H | 2.7 H | in the reaction product of Comparative Example 1, m+n=2.0.

TABLE 3

| | | Reaction Product in Example 3 | | Reaction Product in Example 4 | | Reaction Product Comp. Example 1 | |
|---|---|---|---|---|---|---|---|
| | (ppm) | Found | Calcd. | Found | Calcd. | Found | Calcd. |
| Si—CH$_2$— | 0.6 | 2.1 H | 2.0 H | 2.0 H | 2.0 H | 2.0 H | 2.0 H |
| Si—CH$_2$—CH$_2$— + >NH | 1.5 | 2.6 H | 2.7 H | 2.5 H | 2.3 H | 3.1 H | 3.0 H |
| SiCH$_2$CH$_2$—CH$_2$— + >NCH$_2$CH$_2$N< | 2.4 | 3.9 H | 3.7 H | 3.4 H | 3.3 H | 4.1 H | 4.0 H |
| Si—O—CH$_3$ | 3.5 | 8.9 H | 9.0 H | 8.7 H | 9.0 H | 8.8 H | 9.0 H |

| | | Intensity Ratio | |
|---|---|---|---|
| | (ppm) | Found | Calcd. |
| SiCH$_2$CH$_2$—CH$_2$— + >NCH$_2$CH$_2$N< | 2.4 | 3.6 H | 3.7 H |
| Si—O—CH$_3$ | 3.5 | 5.7 H | 6.0 H |

Structural formula:

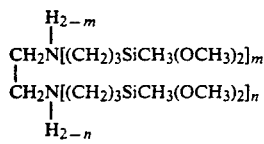

wherein m+n=2.4

Examples 3 and 4, Comparative Example 1

The same procedure as in Example 1 was repeated with the exception that amounts of the raw materials were changed as shown in Table 1, in order to obtain reaction products.

With regard to these reaction products, analyzed values of chlorine present by silver nitrate titration and proton ratios measured by NMR analysis are set forth in Tables 2 and 3, respectively. Moreover, a structural formula is also shown hereinafter.

TABLE 1

| Raw Material | Example 3 | Example 4 | Comp. Ex. 1 |
|---|---|---|---|
| 3-Chloropropyltri-methoxysilane | 2,440 g (12.3) | 2,440 g (12.3) | 2,440 g (12.3) |
| N-2-Aminoethylamino-propyltrimethoxysilane | 1,950 g (8.8) | 1,365 g (6.15) | 2,730 g (12.3) |

Note:
The value in each pair of parentheses denotes mols.

TABLE 2

| | Example 3 | Example 4 | Comp. Ex. 1 |
|---|---|---|---|
| Content of Cl (ppm) | 400 | 570 | 410 |

Structural formula

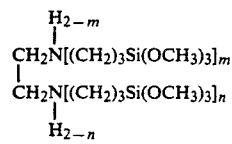

wherein
in the reaction product of Example 3, m+n=2.4, in the reaction product of Example 4, m+n=3.0, and in the reaction product of Comparative Example 1, m+n=2.0.

Example 5

In a 10-liter flask, the inner atmosphere of which was previously replaced with dried nitrogen, was placed 2,270 g (37.8 mols) of ethylenediamine, and 3,000 g (15.1 mols) of 3-chloropropyltrimethoxysilane was added thereto dropwise with stirring over 1 hour, while temperature was maintained at 85° C., and reaction was further carried out for 4 hours. The resulting reaction solution was analyzed by gas chromatography, and it was confirmed that the raw materials were consumed.

After stirring was stopped, the reaction solution was cooled to 50° C., so that it was separated into 2 layers. The upper layer was taken out therefrom and then subjected to quantitative analysis by silver nitrate titration, and it was confirmed that the content of chlorine present was 1,700 ppm, which means that the chlorine atom derived from 3-chloropropyltrimethoxysilane was scarcely present in the upper layer. Furthermore, this upper layer (hereinafter referred to as "reaction product H") was analyzed by NMR, and it was also confirmed that the reaction product H had the following structure.

Structural formula:

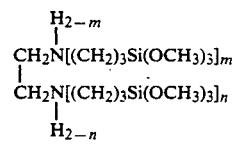

wherein m+n=1.1.
Results of NMR analysis:

| | | Intensity Ratio | |
|---|---|---|---|
| | (ppm) | Found | Calcd. |
| Si—CH$_2$— | 0.6 | 1.8 H | 2.0 H |
| Si—CH$_2$—CH$_2$— + >NH | 1.5 | 4.6 H | 4.6 H |
| SiCH$_2$CH$_2$—CH$_2$— + >NCH$_2$CH$_2$N< | 2.4 | 5.6 H | 5.6 H |
| Si—O—CH$_3$ | 3.5 | 9.0 H | 9.0 H |

Furthermore, in a 5-liter flask, the inner atmosphere of which was previously replaced with dried nitrogen, were placed 500 g (2.10 moles) of this reaction product H, 708 g (3.57 mols) of 3-chloropropyltrimethoxysilane and xylene, and reaction was then performed with stirring at 135° C. for 5 hours. Next, 480 g of a sodium methylate solution was added dropwise thereto over about 2 hours. Afterward, the reaction was further continued for 5 hours, and 207 g of the sodium methylate solution was then added dropwise thereto again over 1 hour to perform the reaction. During this operation, vaporized methanol was distilled off in order to maintain the desired reaction temperature.

After completion of the reaction, secondarily produced sodium chloride was removed from the system, whereby a light brown reaction solution was obtained.

This reaction solution was then analyzed by gas chromatography, and it was confirmed that the raw materials were consumed. According to silver nitrate titration, it was found that the amount of chlorine present was 570 ppm, which means that most of the sodium chloride by-product was removed therefrom.

Furthermore, methanol and xylene were removed from this reaction solution in order to obtain a reaction product. The latter was then analyzed by NMR, and it was confirmed that the product had the following structure.

Structural formula:

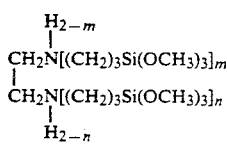

wherein $m+n=2.8$.

Results of NMR analysis:

|  | (ppm) | Intensity Ratio Found | Calcd. |
| --- | --- | --- | --- |
| Si—C$\underline{H_2}$— | 0.6 | 2.1 H | 2.0 H |
| Si—CH$_2$—C$\underline{H_2}$— + >N$\underline{H}$ | 1.5 | 2.3 H | 2.4 H |
| SiCH$_2$CH$_2$—C$\underline{H_2}$— + >NC$\underline{H_2}$C$\underline{H_2}$N< | 2.4 | 3.5 H | 3.4 H |
| Si—O—C$\underline{H_3}$ | 3.5 | 8.9 H | 9.0 H |

Comparative Example 2

In a 5-liter flask, the inner atmosphere of which was previously replaced with dried nitrogen, were placed 500 g (2.10 mols) of the reaction product H obtained in Example 5, 167 g (0.84 mole) of 3-chloropropyltrimethoxysilane and xylene, and reaction was then performed with stirring at 135° C. for 5 hours. Next, 115 g of a sodium methylate solution was added dropwise thereto over about 2 hours. Afterward, the reaction was further continued for 5 hours, and 47 g of the sodium methylate solution was then added dropwise thereto again over 1 hour to perform the reaction. During this operation, vaporized method was distilled off in order to maintain the desired reaction temperature.

After completion of the reaction, secondarily produced sodium chloride was removed from the system, whereby a light brown reaction solution was obtained.

This reaction solution was then analyzed by gas chromatography, and it was confirmed that 3-chloropropyl-trimethoxysilane was consumed. According to silver nitrate titration, it was found that the amount of chlorine present was 470 ppm, which meant that most of the sodium chloride by-product was removed therefrom.

Moreover, methanol and xylene were removed from this reaction solution in order to obtain a reaction product. The latter was then analyzed by NMR, and it was confirmed that the product had the following structure.

Structural formula:

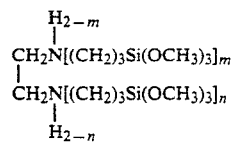

wherein $m+n=1.5$.

Results of NMR analysis:

|  | (ppm) | Intensity Ratio Found | Calcd. |
| --- | --- | --- | --- |
| Si—C$\underline{H_2}$— | 0.6 | 2.2 H | 2.0 H |
| Si—CH$_2$—C$\underline{H_2}$— + >N$\underline{H}$ | 1.5 | 3.7 H | 3.7 H |
| SiCH$_2$CH$_2$—C$\underline{H_2}$— + >NC$\underline{H_2}$C$\underline{H_2}$N< | 2.4 | 4.8 H | 4.7 H |
| Si—O—C$\underline{H_3}$ | 3.5 | 8.8 H | 9.0 H |

Example 6

In a 10-liter flask, the inner atmosphere of which was previously replaced with dried nitrogen, were placed 2,322 g (6.05 mols) of N,N'-bis(trimethoxysilylpropyl)ethylenediamine, 600 g (3.02 mols) of 3-chloropropyltrimethoxysilane and xylene, and reaction was then performed with stirring at 130° C. for 5 hours. Next, 408 g of a sodium methylate solution was added dropwise thereto over about 1 hour. Afterward, the reaction was further continued for 4 hours, and 175 g of the sodium methylate solution was then added dropwise thereto again over 1 hour to perform the reaction. During this operation, vaporized methanol was distilled off in order to maintain the desired reaction temperature.

After completion of the reaction, secondarily produced sodium chloride was removed from the system, whereby a light brown reaction solution was obtained.

This reaction solution was then subjected to silver nitrate titration, and it was found that the amount of chlorine present was 370 ppm, which meant that most of the sodium chloride by-product was removed therefrom.

Furthermore, methanol and xylene were removed from this reaction solution in order to obtain a reaction product. The latter was then analyzed by NMR, and it was confirmed that the product had the following structure.

Results of NMR analysis:

|  | (ppm) | Intensity Ratio Found | Calcd. |
| --- | --- | --- | --- |
| Si—C$\underline{H_2}$— | 0.6 | 2.0 H | 2.0 H |
| Si—CH$_2$—C$\underline{H_2}$— + >N$\underline{H}$ | 1.5 | 2.5 H | 2.6 H |
| SiCH$_2$CH$_2$—C$\underline{H_2}$— + >NC$\underline{H_2}$C$\underline{H_2}$N< | 2.4 | 3.7 H | 3.6 H |
| Si—O—C$\underline{H_3}$ | 3.5 | 8.6 H | 9.0 H |

Structural formula:

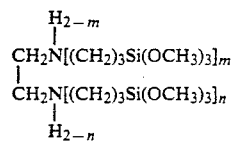

wherein m+n=2.5.

Example 7

In a 10-liter flask, the inner atmosphere of which was previously replaced with dried nitrogen, were placed 2,250 g (4.52 mols) of the methanol-free and xylene-free reaction product (reaction product F) obtained in Example 1 and 2,250 g of methanol, and while the resulting mixture was maintained at 50° C., a mixed solution of 690 g (4.52 mols) of chloromethylstyrene and 690 g of methanol were added dropwise thereto over 4 hours.

Afterward, the reaction was performed at the same temperature for 10 hours. After completion of the reaction, the resulting reaction product was analyzed by gas chromatography, and it was confirmed that the raw materials were consumed.

Moreover, this reaction solution was then subjected to silver nitrate titration, and it was found that 98% or more of chlorine derived from chloromethylstyrene was converted into hydrochloric acid.

Examples 8, 9 and 10

The same procedure as in Example 7 was repeated with the exception that each ratio of materials was changed as shown in Table 4, in order to obtain reaction products.

Each reaction product was then analyzed by gas chromatography, and it was confirmed that most of the raw materials were consumed.

Moreover, each reaction solution was then subjected to silver nitrate titration, it was found that 98% or more of a chlorine atom derived from chloromethylstyrene was converted into hydrochloric acid.

TABLE 4

| Material | Example 8 | Example 9 | Example 10 |
|---|---|---|---|
| Reaction Product F in Example 1 | 2,400 g (4.82) | 2,400 g (4.82) | — |
| Reaction Product F in Example 2 | — | — | 2,400 g (5.83) |
| Methanol (for dissolving reaction product F) | 2,400 g | 2,400 g | 2,400 g |
| Chloromethylstyrene | 660 g (4.33) | 150 g (0.98) | 403 g (2.64) |
| Methanol (for dissolving chloromethylstyrene) | 660 g | 150 g | 403 g |
| Molar Ratio (%) of Chloromethylstyrene to Remaining Active Hydrogen of Reaction Product F | 69.1 | 15.6 | 28.3 |

Note:
The value in each pair of parentheses denotes mol or mols.

Example 11

Pieces of glass cloth were treated with the silane coupling agents obtained in Examples 1 to 10 and the reaction products obtained in Comparative Examples 1 and 2, and epoxy prepregs were made of the treated pieces of glass cloth. Afterward, epoxy laminates were prepared from the epoxy prepregs.

Comparative Examples 3, 4 and 5)

For comparison, epoxy resin laminates were prepared in like manner, using γ-glycidoxypropyltrimethoxysilane (trade name S510 made by Chisso Corp.), 3-(N-styrylmethyl-2-aminoethyl amino)propyltrimethoxysilane hydrochloride and N,N'-bis-(trimethoxysilylpropyl)ethylenediamine. They are respectively Comparative Examples 3,4 and 5.

Afterward, the respective epoxy resin laminates were evaluated, and the results are set forth in Table 5.

In the present invention, performances of the products were evaluated as follows:

Treatment of Glass Cloth

Each of the reaction products obtained in Examples 1, 2, 3, 4, 5 and 6 as well as Comparative Examples 1 and 2 was dissolved in methanol to prepare a solution having a solids content of 50%. Furthermore, the compositions obtained in Examples 7 to 10, γ-glycidoxypropyltrimethoxysilane and N,N'-bis(trimethoxysilylpropyl)ethylenediamine were used directly without any treatment. The compound 3-(N-styrylmethyl-2-aminoethylamino)propyltrimethoxysilane hydrochloride was used in the form of a methanol solution having a solids content was 40%.

The above-mentioned silane coupling agent was dissolved in distilled water, the pH of which was previously adjusted to 4 with acetic acid, in order to prepare a solution having a solids content of 0.5% by weight. Each of γ-glycidoxypropyltrimethoxysilane and N,N'-bis(trimethoxysilylpropyl)ethylenediamine was dissolved in distilled water, the pH of which was previously adjusted to 4 with acetic acid, in order to prepare a solution having a solids content was 0.5% by weight. Moreover, 3-(N-styrylmethyl-2-aminoethylamino)-propyltrimethoxysilane hydrochloride was dissolved in distilled water, the pH of which was previously adjusted to 2.5 with formic acid, in order to prepare a solution having a solids content of 0.5% by weight.

Each piece of heat cleaned glass cloth (glass fiber fabric made by Nitto Boseki Co., Ltd.; trade name WEA-18K) was immersed in each of the above-mentioned solutions and then squeezed by squeeze rolls, followed by drying at 110° C. for 10 minutes.

Preparation of Laminate Specimens

Pieces of surface-treated glass cloth were impregnated with G-10 type epoxy resin (trade name Epicoat 1001 made by Shell Petrochemical Co., Ltd.) and then dried at 130° C. for 15 minutes in order to form prepregs. Eight sheets of these prepregs were superposed upon each other, and these prepregs were then sandwiched between two copper foils. Afterward, the sandwiched prepregs were heated at 175° C. for 60 minutes under a load of 30 kg/cm$^2$ so as to perform molding. The copper foils were then removed therefrom by etching, thereby preparing specimens.

(1) Boiling Water Absorption Rate

In accordance with a test procedure of JIS C-6481, each laminate specimen, was boiled for a period of 5 to 20 hours, and afterward the water absorption rate was measured.

(2) Soldering Heat Resistance Test

Each laminate specimen was boiled in a pressure cooker at 133° C. and then immersed in a solder bath at 280° C. for 20 seconds. After the specimen was taken out therefrom, blister or peeling on the specimen were observed. The boiling time until the occurrence of these drawbacks was regarded as the soldering heat resistance time.

(3) Heat Shock Resistance

Each laminate specimen was immersed in liquid nitrogen for about 1 minute, and immediately it was then floated on a solder bath at 280° C. Afterward, damage to the specimen was observed, and evaluation was made on the basis of the following standards.

⊙ . . . No. damage was observed.
○ . . . Spot-like damage occurred slightly.
Δ . . . A great deal of spot-like damage occurred.
X . . . Spot-like damage occurred all over the surface.

(4) Resin Impregnation Characteristics (prepreg)
Resin impregnation states were observed, and evaluation was made on the basis of the following standards.

⊙ . . . Transparency was very good.
○ . . . Transparency was good.
Δ . . . Transparency was slightly bad.
X . . . Transparency was bad.

(5) Methylene Chloride Resistance
In accordance with JIS C-6481, each laminate specimen was immersed in methylene chloride at 20° C. for 1 hour, and evaluation was then made by observing the appearance of the specimen.

TABLE 5

| | Content (%) of Resin in Laminate | Water Absorption Rate (%) at Each Boiling Time | | | Solder Heat Resistance Time (min) | Heat Shock Resistance | Impregnation of Resin (prepreg) | Methylene Chloride Resistance |
|---|---|---|---|---|---|---|---|---|
| | | 5 h. | 10 h. | 20 h. | | | | |
| Example 1 | 41.2 | 0.52 | 0.63 | 0.84 | 120 | ⊙ | ○ | not changed |
| Example 2 | 41.2 | 0.51 | 0.63 | 0.81 | 120 | ⊙ | ○ | not changed |
| Example 3 | 40.8 | 0.52 | 0.64 | 0.84 | 115 | ⊙ | ○ | not changed |
| Example 4 | 40.5 | 0.51 | 0.63 | 0.83 | 115 | ⊙ | ○ | not changed |
| Example 5 | 40.9 | 0.52 | 0.61 | 0.81 | 120 | ⊙ | ○ | not changed |
| Example 6 | 41.0 | 0.51 | 0.62 | 0.82 | 115 | ⊙ | ○ | not changed |
| Example 7 | 40.8 | 0.51 | 0.61 | 0.81 | 120 | ⊙ | ⊙ | not changed |
| Example 8 | 41.0 | 0.50 | 0.60 | 0.80 | 120 | ⊙ | ⊙ | not changed |
| Example 9 | 40.4 | 0.51 | 0.61 | 0.81 | 120 | ⊙ | ⊙ | not changed |
| Example 10 | 40.8 | 0.52 | 0.61 | 0.83 | 120 | ⊙ | ⊙ | not changed |
| Comparative Example 1 | 40.7 | 0.62 | 0.67 | 0.93 | 100 | Δ | ○ | slightly changed |
| Comparative Example 2 | 40.9 | 0.60 | 0.71 | 0.91 | 100 | Δ | ○ | slightly changed |
| Comparative Example 3 | 40.9 | 0.67 | 0.73 | 1.02 | 75 | X | Δ | a little changed |
| Comparative Example 4 | 41.3 | 0.63 | 0.71 | 1.01 | 105 | Δ | ⊙ | slightly changed |
| Comparative Example 5 | 41.1 | 0.62 | 0.68 | 0.92 | 100 | Δ | ○ | slightly changed |

As shown in Table 5, the products prepared in the respective examples according to the present invention have much better results than the products prepared in the respective comparative examples, particularly 3-(N-styrylmethyl-2-aminoethylamino)propyltrimethoxysilane hydrochloride which is presently often used as a silane coupling agent for printed-circuit boards, in all points of water absorption, soldering heat resistance, heat shock resistance and methylene chloride resistance.

What is claimed is:

1. A glass fiber product for laminates comprising a glass fiber material treated with a silane coupling agent prepared by reacting 2.3 to 4.0 mols of a haloalkylalkoxysilane with 1 mole of a diamine having N atoms to which 4 active hydrogen atoms are bound.

2. A glass fiber product for laminates comprising a glass fiber material treated with a silane coupling agent prepared by reacting 1.3 to 3.0 mols of a haloalkylalkoxysilane with 1 mol of a diamine having N atoms to one of which one alkylsilyl group is bound and to the residual bonds of which 3 active hydrogen atoms are bound.

3. A glass fiber product for laminates comprising a glass fiber material treated with a silane coupling agent prepared by reacting 0.3 to 2.0 mols of a haloalkylalkoxysilane with 1 mol of a diamine having N atoms to each or either of which 2 alkylsilyl groups are bound and to each or either of which 2 active hydrogen atoms are bound.

4. A glass fiber product for laminates comprising a glass fiber material treated with a silane coupling agent prepared by reacting a halomethylstyrene with (a) a reaction product obtained by reacting 2.3 to 3.5 mols of a haloalkylalkoxysilane with 1 mol of a diamine having N atoms to which 4 active hydrogen atoms are bound, (b) a reaction product obtained by reacting 1.3 to 2.5 mols of a haloalkylalkoxysilane with 1 mol of a diamine having N atoms to one of which one alkylsilyl group is bound and to the residual bonds of which 3 active atoms are bound or (c) a reaction product obtained by reacting 0.3 to 1.5 mols of a haloalkylalkoxysilane with 1mol of a diamine having N atoms to each or either of which 2 active hydrogen atoms are bound and to each or either of which 2 alkylsilyl groups are bound, the amount of said halomethylstyrene being not more than 80 mol% of mol amounts given by subtracting the mols of said haloalkylalkoxysilane used from the mols of said active hydrogen atoms of said diamine used.

5. A glass fiber product for laminates comprising a glass fiber material treated with a silane coupling agent according to claim 4 wherein said halomethylstyrene is chloromethylstyrene.

6. A glass fiber product for laminates comprising a glass fiber material treated with a silane coupling agent according to claim 1 wherein said haloalkylalkoxysilane is a compound represented by the formula

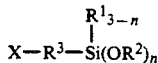

wherein each of $R^1$ and $R^2$ are independently a substituted or unsubstituted alkyl group, an aryl group or an alkenyl group having 1 to 6 carbon atoms, $R^3$ is a straight-chain or branched alkylene group having 1 to 6 carbon atoms, n is 1, 2 or 3, and X is a halogen atom.

7. A glass fiber product for laminates comprising a glass fiber material treated with a silane coupling agent according to claim 2 wherein said haloalkylalkoxysilane is a compound represented by the formula

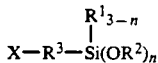

wherein each of $R^1$ and $R^2$ are independently a substituted or unsubstituted alkyl group, an aryl group or an alkenyl group having 1 to 6 carbon atoms, $R^3$ is a straight-chain or branched alkylene group having 1 to 6 carbon atoms, n is 1, 2 or 3, and X is a halogen atom.

8. A glass fiber product for laminates comprising a glass fiber material treated with a silane coupling agent according to claim 3 wherein said haloalkylalkoxysilane is a compound represented by the formula

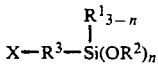

wherein each of $R^1$ and $R^2$ are independently a substituted or unsubstituted alkyl group, an aryl group or an alkenyl group having 1 to 6 carbon atoms, $R^3$ is a straight-chain or branched alkylene group having 1 to 6 carbon atoms, n is 1, 2 or 3, and X is a halogen atoms.

9. A glass fiber product for laminates comprising a glass fiber material treated with a silane coupling agent according to claim 4 wherein said haloalkylalkoxysilane is a compound represented by the formula

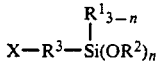

wherein each of $R^1$ and $R^2$ are independently a substituted or unsubstituted alkyl group, an aryl group or an alkenyl group having 1 to 6 carbon atoms, $R^3$ is a straight-chain or branched alkylene group having 1 to 6 carbon atoms, n is 1, 2 or 3, and X is a halogen atom.

10. A glass fiber product for laminates comprising a glass fiber material treated with a silane coupling agent according to claim 5 wherein said haloalkylalkoxysilane is a compound represented by the formula

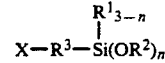

wherein each of $R^1$ and $R^2$ are independently a substituted or unsubstituted alkyl group, an aryl group or an alkenyl group having b 1 to 6 carbon atoms, $R^3$ is a straight-chain or branched alkylene group having 1 to 6 carbon atoms, n is 1, 2 or 3, and X is a halogen atom.

11. A glass fiber product for laminates according to claim 1 wherein said silane coupling agent includes at least two silyl groups per molecule.

12. A glass fiber product for laminates according to claim 2 wherein said silane coupling agent includes at least two silyl groups per molecule.

13. A glass fiber product for laminates according to claim 3 wherein said silane coupling agent includes at least two silyl groups per molecule.

14. A glass fiber product for laminates according to claim 4 wherein said silane coupling agent includes at least two silyl groups per molecule.

15. A glass fiber product for laminates according to claim 4 wherein said silane coupling agent comprises the product of a reaction between a halomethylstyrene with the reaction product obtained from the reaction of 2.3 to 3.5 mols of a haloalkylalkoxysilane with 1 mole of a diamine having N atoms, to which four active hydrogen atoms are bound.

16. A glass fiber product for laminates according to claim 4 wherein said silane coupling agent comprises the reaction product of a halomethylstyrene with the reaction product obtained from the reaction of 1.3 to 2.5 mols of a haloalkylalkoxysilane with 1 mol of a diamine having N atoms, to one of which one alkylsilyl group is bound and to the residual bonds of which three active hydrogen atoms are bound.

17. A glass fiber product for laminates according to claim 4 wherein said silane coupling agent comprises the reaction product of a halomethylstyrene with the reaction product obtained from the reaction of 0.3 to 1.5 mols of a haloalkyl- alkoxysilane with 1 mol of a diamine having N atoms, to each or either of which two active hydrogen atoms are bound and to each or other of which two alkylsilyl groups are bound.

* * * * *

UNITED STATES PATENT AND TRADEMARK OFFICE
CERTIFICATE OF CORRECTION

PATENT NO. : 5,069,971

DATED : December 3, 1991

INVENTOR(S) : Waketa et al.

It is certified that error appears in the above-identified patent and that said Letters Patent is hereby corrected as shown below:

Column 17, line 64, change "mole" to --mol--;

Column 18, line 51, after "active" insert --hydrogen--;

line 53, change "1mol" to --1 mol--.

Column 19, line 39, change "atoms" to --atom--.

Column 20, line 14, delete "b";

line 33, change "mole" to --mol--;

line 50, change "other" to --either--.

Signed and Sealed this

Thirtieth Day of March, 1993

*Attest:*

STEPHEN G. KUNIN

*Attesting Officer*      *Acting Commissioner of Patents and Trademarks*